(12) United States Patent
Choi et al.

(10) Patent No.: US 9,220,668 B2
(45) Date of Patent: Dec. 29, 2015

(54) COSMETIC COMPOSITION

(71) Applicant: S & V Technologies GmbH, Henningsdorf (DE)

(72) Inventors: SooWhan Choi, Berlin (DE); Said Hilton, Dusseldorf (DE); Maricica Munteanu, Berlin (DE)

(73) Assignee: S & V Technologies AG, Henningsdorf (DE)

( * ) Notice: Subject to any disclaimer, the term of this patent is extended or adjusted under 35 U.S.C. 154(b) by 0 days.

(21) Appl. No.: 13/848,261

(22) Filed: Mar. 21, 2013

(65) Prior Publication Data

US 2013/0217767 A1 Aug. 22, 2013

Related U.S. Application Data

(63) Continuation-in-part of application No. PCT/EP2011/066420, filed on Sep. 21, 2011.

(30) Foreign Application Priority Data

Sep. 21, 2010 (EP) .................................... 10010096

(51) Int. Cl.
*A61K 8/37* (2006.01)
*A61Q 7/00* (2006.01)
*A61K 8/69* (2006.01)

(52) U.S. Cl.
CPC ... *A61K 8/37* (2013.01); *A61K 8/69* (2013.01); *A61Q 7/00* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 2007/0053984 A1* | 3/2007 | Spann-Wade et al. | 424/486 |
| 2008/0152680 A1* | 6/2008 | Brown et al. | 424/401 |
| 2009/0136435 A1* | 5/2009 | Mulvanerty | 424/59 |
| 2010/0111883 A1* | 5/2010 | Vitins et al. | 424/59 |
| 2010/0158980 A1* | 6/2010 | Kopczynski et al. | 424/426 |
| 2010/0216877 A1 | 8/2010 | Kshirsagar et al. | |
| 2011/0152264 A1 | 6/2011 | Reunamaki et al. | |
| 2011/0152373 A1 | 6/2011 | Ropo | |
| 2011/0313038 A1 | 12/2011 | Lallemand et al. | |
| 2011/0319488 A1 | 12/2011 | Lallemand et al. | |

FOREIGN PATENT DOCUMENTS

| | | |
|---|---|---|
| EP | 0435682 A2 | 7/1991 |
| EP | 2127638 A1 | 12/2009 |
| EP | 2228057 A1 | 9/2010 |
| EP | 2228058 A1 | 9/2010 |
| WO | 2010027040 A1 | 3/2010 |

OTHER PUBLICATIONS

International Search Report for PCT/EP2011/066420 dated Apr. 5, 2013.
European Search Report for EP10010096 dated Feb. 25, 2011.

* cited by examiner

*Primary Examiner* — David J Blanchard
*Assistant Examiner* — Sarah Chickos
(74) *Attorney, Agent, or Firm* — Millen, White, Zelano & Branigan, P.C.

(57) ABSTRACT

The present invention concerns a cosmetic composition comprising the following fluorinated analog of prostaglandin F2α: The cosmetic composition may further comprise a complexing agent and/or a humectant. The present invention further relates to a cosmetic kit, comprising the cosmetic composition and an applicator for application thereof.

7 Claims, 3 Drawing Sheets

——— reference line

——— reference line

COSMETIC COMPOSITION

The present invention relates to cosmetic compositions comprising tafluprost, in particular for stimulating hair growth, and a cosmetic kit comprising the cosmetic composition as well as an applicator.

Prostaglandines are a group of lipid compounds, which are found in various bodily tissues and organs and share a number of structural features, including a 5-membered ring. Prostaglandines and some of their synthetic analogs have various physiological functions and have been put to pharmacological use in applications reaching from the induction of childbirth to the treatment of glaucoma.

Bimatoprost is just one example of a prostaglandin analog used in a commercially available ophthalmic solution to control the progression of glaucoma and treat ocular hypertension. Tafluprost is another example of a prostaglandin analog, which has proven to be useful in ophthalmic applications. Clinical studies have demonstrated its efficacy at decreasing intraocular pressure in patients with open-angle glaucoma or ocular hypertension.

The use of such prostaglandin analogs in ophthalmic solutions, however, is associated with various undesirable side effects, such as discolouration of the iris and darkening of the inner eyelids. However, there is even a positive side effect, which is the increased growth of eyelashes. This observation has led to the development of cosmetic compositions comprising bimatoprost and the use of bimatoprost in the stimulation of hair growth allowing treatment of alopecia and related conditions. Methylamido Dihydro Noralfaprostal is a further prostaglandin analog that has been known for its use in cosmetic applications relating to promoting the growth of eyelashes.

U.S. Pat. No. 7,351,404, for instance, relates to methods for stimulating hair growth in mammals comprising the application of a specific class of prostaglandin analogs and encompasses cosmetic applications. Bimatoprost is an exemplary embodiment of this class of compounds.

Since the same or similar concentrations of prostaglandin analog are used in both ophthalmic solutions and cosmetic compositions, side effects such discolouration of the iris and darkening of the eyelids also occur in the cosmetic applications. They are, of course, undesirable and even more perturbing in a purely aesthetic application intended to improve rather than deteriorate the visual impression. International patent application published as WO 2009/151828 suggests the concurrent use of a "lightening and/or neutralizing agent" with hair growth stimulating agents such as prostaglandin analogs, which are supposed to neutralize any darkening or change of the skin and/or eyes in response to the application of the hair growth stimulating agents. However, the addition of such substances not only increases the complexity of the composition but also increases the risk of additional side effects.

Due to the occurrence of the above-mentioned side effects, it does not appear feasible to increase the concentration of the prostaglandin analogs to any significant extent beyond that used in ophthalmic solutions, thus somewhat limiting the desired effect.

In light of the above, it is an object of the present invention to provide an effective hair growth stimulating cosmetic composition, which avoids or at least diminishes the above-mentioned side effects.

It is also an object of the present invention to provide a hair growth stimulating cosmetic composition having improved efficacy.

The above objects are solved by a cosmetic composition comprising tafluprost. Tafluprost ($C_{25}H_{34}F_2O_5$, $M_r$=452.5 g/mol) is a fluorinated analog of prostaglandin F2α, which is represented by the formula (I) below:

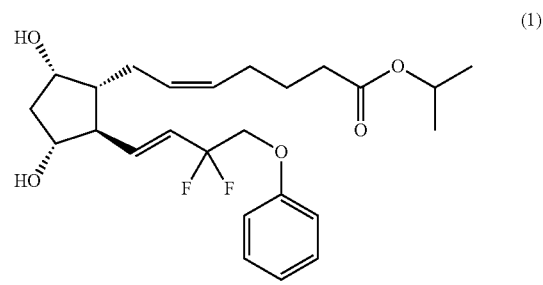 [SMILES: CC(C)OC(=O)CCC/C=C\C[C@@H]1[C@@H](/C=C/C(F)(F)COc2ccccc2)[C@H](O)C[C@@H]1O]

As mentioned before, tafluprost has proven efficacy in the treatment of glaucoma and ocular hypertension and is commercially available as Saflutan® eyedrops in various countries. However, just like with other prostaglandin analogs, increased pigmentation of the iris and eyelids and local darkening of the skin are among the reported side effects.

It is therefore surprising that a cosmetic composition comprising tafluprost does not only have excellent efficacy but also shows much less than would be expected of the above mentioned side effects.

Tafluprost, as used herein, comprises the molecule having the structure illustrated above by formula (I) as well as any salts and solvates thereof that are acceptable for cosmetic, and in particular topical application. For ease of reference, it is simply referred to tafluprost herein.

In a particularly preferred embodiment, the cosmetic composition comprises a complexing agent for forming a complex with the tafluprost. Particularly preferred are those complexing agents that provide a slow release of the tafluprost from the complex and thus the composition. Examples of suitable complexing agents encompass cyclodextrin and derivatised cyclodextrin. Cyclodextrin derivatives comprise, for instance hydroxyalkyl-derivatives of cyclodextrin, ethers of cyclodextrins, sulfoalkylethers of cyclodextrin, alkylated cyclodextrin, such as methylated cyclodextrin, and the like. α- and β-Cyclodextrin, also known as cycloamylose, either alone or in combination, are particularly preferred complexing agents. α-Cyclodextrin is most preferred.

First test results of the inventive composition indicate that the use of a complexing agent, in particular a cyclodextrin, is highly beneficial. It increases efficacy whilst minimizing side effects.

Without wishing to be bound by theory, it is stipulated that the observed good efficacy is due to tafluprost being released from the complex in a modified manner, thus providing for extended action. This could also explain the absence of noticeable side effects.

In exemplary embodiments, tafluprost and the complexing agent are comprised in a molar ratio from 1:1 (tafluprost:complexing agent) to 1:10 (tafluprost:complexing agent), for instance from 1:1 (tafluprost:complexing agent) to 1:6 (tafluprost:complexing agent), preferably from 1:1 (tafluprost:complexing agent) to 1:4 (tafluprost:complexing agent) and most preferably 1:1 (tafluprost:complexing agent) to 1:2 (tafluprost:complexing agent). Thus, it is preferred that the complexing agent is comprised in an at least equimolar amount or in excess.

The cosmetic composition according to the present invention may comprise tafluprost in an amount of up to 0.0025 wt.-%, preferably in an amount from 0.0002 to 0.0018 wt.-%, more preferably in an amount from 0.0008 to 0.0014 wt.-%, based on the total weight of the composition. Preferably, 0.0012 wt.-% or less, and more preferably 0.001 wt.-% or less tafluprost are used in the inventive cosmetic compositions.

In further preferred embodiments, a humectant is included in the cosmetic composition. A humectant is a hygroscopic substance that serves to retain moisture in the cosmetic composition. In the present case, the use of a humectant serves to retain some moisture in the cosmetic composition even when the cosmetic composition has substantially dried on the skin, i.e. volatile compounds have evaporated.

The cosmetic composition's ability to retain moisture upon topical application that is associated with the use of a humectant is believed to be a further reason for the improved efficacy of the tafluprost containing cosmetic compositions.

It is further stipulated that the combination of a complexing agent, such as cyclodextrin, and a humectant in the cosmetic compositions according to the present invention provides a synergistic effect: The retention of moisture enables the modified release of tafluprost from the complex to occur over an extended period of time. On the one hand, the humectant provides a suitable (moist) environment for the release of tafluprost from the complex, on the other hand, it is presumed that it has a direct impact on the release and thus absorption of tafluprost.

Preferably, the humectant is contained in an amount of up to 25 wt.-%, such as up to 10 wt.-%, more preferably from 0.05 to 5 wt.-%, for instance from 0.1 to 3 wt.-% and most preferably from 0.2 to 1.3 wt.-%, based on the total weight of the composition.

The humectant may comprise only one compound or a mixture of compounds having the required hygroscopic properties.

Suitable humectants for use in the cosmetic industry are known in the art. By way of example, glycerol, propylene glycol, sugar polyols, such as sorbitol and xylitol may be mentioned, as well as polymeric polyols, polysaccharides, or natural extracts, such as urea and glycosaminoglycans.

Preferably, a hyaluronate and/or hyaluronic acid is used as the humectant or as part of the humectant. Hyaluronate and hyaluronic acid have the added advantage of promoting water retention within the skin thus improving the appearance or the skin. Hyaluronates or hyaluronic acid may also improve absorption of tafluprost or a complex comprising tafluprost, respectively. Any cosmetically acceptable hyaluronate (salt of hyaluronic acid) may be used, such as alkali or earth alkali metal salts, including sodium hyaluronate. Sodium hyaluronate is particularly preferred.

The combination of a cyclodextrin, such as α-cyclodextrin, and hyaluronic acid or salt thereof (hyaluronate) has been found to be very advantageous.

Preferably, the cosmetic composition according to the present invention is based on an aqueous system. An aqueous system, as used herein, refers to a system wherein water is the major solvent, i.e. makes up more than 50 wt.-%, preferably more than 70 wt.-%, 80 wt.-% or 90% wt.-% of any solvents used. Water may be the only solvent. In other embodiments, an alcohol, preferably ethanol, may also be comprised in the aqueous system. However, the most preferred embodiments of the composition are free of alcohol, even ethanol, in order to avoid any possible irritation of the skin or the eye. Further preferably, the cosmetic composition comprises an aqueous buffer, which is suitable to adjust the pH of the cosmetic composition to a desired value. Any buffer suitable for cosmetic application to the skin may be used, such as phosphate buffer, acetate buffer and ammonium buffer. The buffer advantageously has a pH in the range of from 7.00 to 7.80. Preferably the cosmetic composition has a pH value in the range of from 7.30 to 7.50, preferably from 7.35 to 7.45 and most preferably from 7.37 to 7.42. If necessary, the pH may be adjusted by addition of a suitable acid or base.

The aqueous phase, including the buffer, can make up from at least 50 wt.-%, for instance at least 75 wt.-% and more preferred at least 90 wt.-% of the composition, for example. Preferably, the aqueous phase, including the buffer, makes up between 98.20 and 98.52 wt.-% of the composition, for instance between 98.30 and 98.49 wt.-%, more preferably at least 98.49 wt.-%, based on the total weight of the composition.

The cosmetic composition of the present invention may be in the form of a solution, in particular an aqueous solution, an emulsion, a gel, an ointment, a cream, a lotion or the like. An aqueous solution and a gel are particularly preferred.

In preferred embodiments of the cosmetic composition according to the present invention, the cosmetic composition takes the form of a gel, in particular an only slightly viscous gel. The gel preferably has a slightly higher viscosity than water. Preferred herein are compositions having a viscosity of more than 500 mPa·s, more preferably more than 1200 mPa·s and preferably less than 5000 mPa·s at a temperature of 20° C., when viscosity is measured by a rheometer, for instance measured according to Ph. Eur. Edition 4 (2002), Chapter 2.2.10 (4.00/2.02.10.00). Preferably, the gel is an aqueous gel, i.e. based on an aqueous system, as described above.

In order to adjust the consistency of the gel, or more generally to adjust the viscosity of the composition, one or more thickening agents may be added. A thickening agent, as used herein, is a compound or mixture of compounds typically of high molecular weight, which is capable of increasing the viscosity of water and aqueous solutions. The thickening agent may be an inorganic thickening agent, such as bentonite and the like. Examples of suitable thickening agents comprise polymers such as polyethylene glycol, polyacrylic acid and natural products, such as gums and the like. The thickening agent is preferably a polysaccharide, such as sodium alginate, gum arabic, cellulose derivatives including cellulose ethers, and xanthan. Xanthan is particularly preferred. Transparent xanthan is particularly preferred.

It has been found that xanthan, and transparent xanthan in particular, does not only provide for a desirable consistency of the cosmetic composition but also leads to faster drying.

In exemplary embodiments, a thickening agent or mixture thereof may be comprised in amounts ranging from 1 to 10 wt.-%, based on the total weight of the composition, preferably 0.05 to 5 wt.-%, more preferably 0.1 to 2.5 wt.-%. In an exemplary embodiment, a thickening agent, most preferably xanthan, is comprised in an amount of 0.1 to 0.5 wt.-%.

Cosmetic compositions comprising tafluprost, a complexing agent, in particular a cyclodextrin, a humectant, in particular hyaluronic acid or a hyaluronate, and a thickening agent, in particular xanthan, and preferably in an aqueous buffer system are particularly preferred.

In other exemplary embodiments, the addition of a complexing agent and a humectant may be sufficient to provide the desired viscosity, in which case the composition may be free from any further thickening agent.

The cosmetic composition may comprise a preservative. Any preservative suitable for use in cosmetic applications may be used that is able to prevent growth of bacteria, fungi and/or viruses. Examples of suitable preservatives include phenoxyethanol, chlorohexidine, phenylmercuric salts including nitrate, chloride, acetate, borate, chlorobutanol, silver nano particles and the like. The use of phenoxyethanol is particularly preferred.

A preservative may be used in the cosmetic compositions in an amount of up to 5 wt.-%, for instance up to 2 wt.-%, preferably in amounts ranging from 0.05 to 1.0 wt.-% and more preferably 0.4 to 0.5 wt.-%, based on the total weight of the composition.

In a preferred embodiment, the composition comprises one or more, and preferably all, of the following ingredients in the indicated percentages, based on the total weight of the composition:

|  | Preferred embodiment [wt.-%] | Exemplary embodiment [wt.-%] |
|---|---|---|
| Tafluprost | 0.002 to 0.0018 | 0.008 to 0.0014 |
| Buffer (including water) | >90 | 98.197 to 98.518 |
| Cyclodextrin | 0.0015 to 0.5 | 0.0022 to 0.1810 |
| Hyaluronate or hyaluronic acid | 0.1 to 3 | 0.2 to 1.3 |
| Preservative | <1.5 | 0.4 to 0.5 |
| Thickening agent, in particular xanthan | 0.1 to 2.5 | 0.19 to 0.30 |
| Ethanol | 0.0 to 3.5 | 2.8 to 3.1 |

The cosmetic composition may contain various other ingredients that are beneficial in the cosmetic application, such as vitamins, nourishing oils, mineral salts, plant extracts, amino acids and the like. However, embodiments are preferred in which the composition is free from any of these ingredients as these prevent the occurrence of any undesired interactions among the ingredients.

The cosmetic composition according to the present invention is particularly suitable for stimulating the growth of hair, preferably eyelashes and/or eyebrows. Volume, texture and/or density of eyelashes, as well as other hair, can be improved by the inventive composition.

The term "cosmetic composition", as used herein, shall exclude any ophthalmic compositions. It preferably does so by containing one or more components of such nature or in such amounts that render the composition not ophthalmically acceptable or having a pH or osmolality that renders the composition not ophthalmically acceptable. Preferably, it contains tafluprost in addition to one or more cosmetic excipients that are not ophthalmically compatible or are comprised in amounts that are not ophthalmically compatible.

The present invention further provides a cosmetic kit, comprising a cosmetic composition as described before and an applicator for applying the cosmetic composition. The applicator advantageously allows a defined application of the composition to the skin. The term "applicator", as used herein, encompasses any artificial device suitable for applying the cosmetic composition directly to the skin, and thus excludes human bodily parts or the container in which the composition is contained as such, like a flask or bottle for dispensing droplets. However, the applicator may be provided in combination with the container or even integrally formed therewith. The applicator is designed for direct application of the composition to the skin and thus direct contact with the skin and/or eyelashes. The applicator may be a brush, for instance.

The cosmetic composition according to the present invention thus involves the use of the inventive composition for cosmetic application. The term "cosmetic" shall exclude suitability for ophthalmic application. The present invention also relates to a cosmetic method for stimulating growth of hair, comprising topical application, i.e. application of the composition directly to the skin. For promoting the growth of eyelashes, the composition is advantageously directly applied to the skin of at least the upper eyelid. Thus, the cosmetic composition is suitable for application to the skin and preferably the eyelids.

The cosmetic composition is intended for application once a day, preferably every day, and preferably for a period of at least six weeks.

BRIEF DESCRIPTION OF DRAWINGS

The invention is further described by way of an exemplary embodiment with reference to the figures, wherein.

The entire disclosure of all applications, patents and publications, cited herein and copending International Application No. PCT/EP2011/066420, filed Sep. 21, 2011 are incorporated herein by reference.

EXAMPLE 1

A cosmetic composition is made up of the following components:

|  | Amount [g] |
|---|---|
| Aqueous phase | |
| Phosphate buffer, pH = 7.4 | 94.084 |
| Sodium hyaluronate | 0.200 |
| Phenoxyethanol | 0.500 |
| Xanthan transparent | 0.200 |
| Ethanol | 3.000 |
| Active ingredient phase | |
| Tafluprost | 0.001 |
| α-Cyclodextrin | 0.010 |
| Water | 2.000 |
| Total | 100.000 |

The above composition is made by mixing the indicated ingredients. The composition was used for application once a day by application of the composition with a thin brush directly to the skin of the upper eyelid by a user over a period of 4 weeks.

Figure 1:
FIG. 1 shows a photograph of an user's eye and eyelashes before commencing treatment with the cosmetic composition according to Example 1.
Figure 2:
FIG. 2 shows a photograph of the same user's eye and eyelashes after 4 weeks of treatment with the cosmetic composition according to Example 1.

FIGS. 1 and 2 illustrate that the user's eyelashes did not only become denser, but also longer and thicker after treatment. In addition, no noticeable skin darkening of the like was observed.

EXAMPLE 2

A cosmetic composition is made up of the following components:

|  | amount [g] |
|---|---|
| Phosphate buffer, pH = 7.4 | 96.939 |
| Sodium hyaluronate | 0.550 |
| Phenoxyethanol | 0.500 |
| Tafluprost | 0.001 |
| α-Cyclodextrin | 0.010 |
| Water | 2.000 |
| Total | 100.000 |

The above mentioned composition is made by mixing of the indicated ingredients. The composition is used for application once a day by application of the composition with a thin brush directly to the skin of the upper eyelid by a user over a period of 4 weeks.

Figure 3:
FIG. 3 shows a photograph of an user's eye and eyelashes (different from FIGS. 1 and 2) before commencing treatment with the cosmetic composition according to Example 2.
Figure 4:
FIG. 4 shows a photograph of the same user's eye and eyelashes as in FIG. 3 after 4 weeks of treatment with the cosmetic composition according to Example 2.
Figure 5:
FIG. 5 shows a photograph of another user's eye and eyelashes before commencing treatment with the cosmetic composition according to Example 2.
Figure 6:
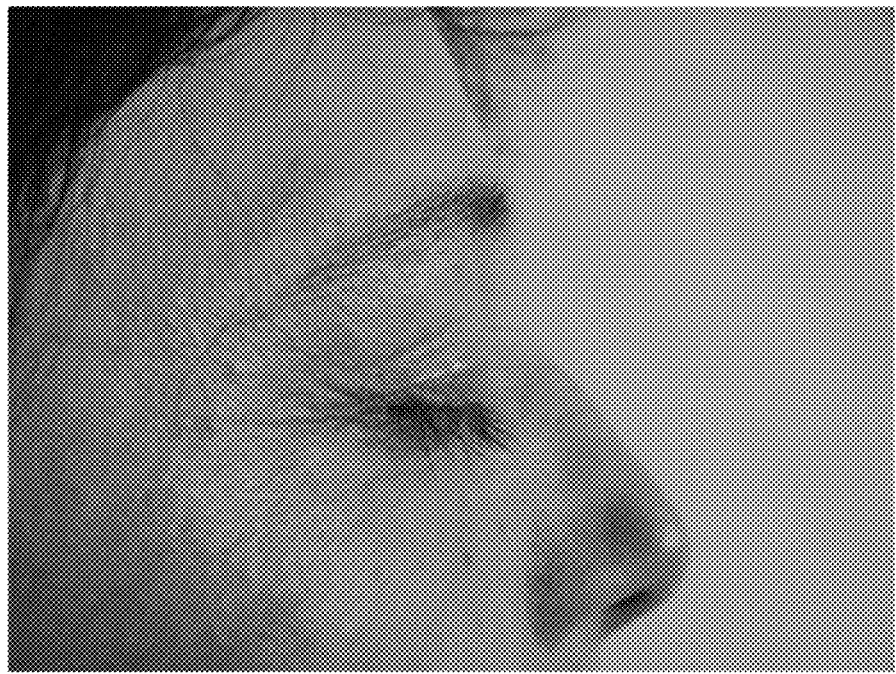
FIG. 6 shows a photograph of the same user's eye and eyelashes as in FIG. 5 after 4 weeks of treatment with the cosmetic composition according to Example 2.

Further experiments and comparative studies confirm the above described effects. FIGS. 3/4 and 5/6 also show the results of an application of the composition according to example 2 in test persons. The pairs of figures show the same proband before (FIGS. 3 and 5) and after (FIGS. 4 and 6) the application over 4 weeks.

The described effect of the composition can be seen in the vast majority of volunteers (ca. 90-95%) der. None of the probands showed any sign of side effect. This is a surprisingly positive result which could not be expected from the prior art.

The invention claimed is:

1. A cosmetic composition comprising:

| aqueous buffer pH 7.4 | 96.939 g |
|---|---|
| sodium hyaluronate | 0.550 g |
| phenoxyethanol | 0.500 g |
| tafluprost | 0.001 g |
| α-cyclodextrin | 0.010 g |
| water | 2.000 g |
| total | 100.000 g. |

2. The cosmetic composition according to claim 1, which is adapted for stimulating the growth of hair.

3. The cosmetic kit, comprising a cosmetic composition according to claim 1 together with an applicator.

4. A cosmetic kit according to claim 3 in which the applicator is a brush.

5. A method of stimulating hair growth of a human subject comprising applying said composition according to claim 1 to said human subject.

6. A method of stimulating hair growth of the eyebrows and/or eyelashes of a human subject comprising applying the composition according to claim 1 to said eyebrows and/or eyelashes.

7. The cosmetic composition according to claim 2, wherein the hair is eyelashes and/or eyebrows.

* * * * *